United States Patent [19]
DeCampli

[11] Patent Number: 5,571,127
[45] Date of Patent: Nov. 5, 1996

[54] SCALPEL HANDLE HAVING RETRACTABLE BLADE SUPPORT AND METHOD OF USE

[76] Inventor: William M. DeCampli, 8 Heritage Ct., Atherton, Calif. 94027

[21] Appl. No.: 401,018

[22] Filed: Mar. 8, 1995

[51] Int. Cl.$^6$ .................................................. A61B 17/32
[52] U.S. Cl. ............................................ 606/167; 30/125
[58] Field of Search .................................. 606/167, 170, 606/172; 30/125, 162, 335

[56] References Cited

U.S. PATENT DOCUMENTS

| | | | |
|---|---|---|---|
| 3,192,624 | 7/1965 | Gringer | 30/162 |
| 5,201,748 | 4/1993 | Newman et al. | 606/167 |
| 5,211,652 | 5/1993 | Derbyshire | 606/182 |
| 5,258,001 | 11/1993 | Corman | 606/167 |
| 5,275,606 | 1/1994 | Abidin et al. | 606/167 |
| 5,292,329 | 3/1994 | Werner | 606/167 |
| 5,301,428 | 4/1994 | Wilcox | 30/162 |
| 5,303,474 | 4/1994 | Keklak et al. | 30/162 |
| 5,330,492 | 7/1994 | Haugen | 606/167 |
| 5,330,493 | 7/1994 | Haining | 606/167 |
| 5,342,379 | 8/1994 | Volinsky | 606/167 |
| 5,344,424 | 9/1994 | Roberts et al. | 606/167 |
| 5,377,413 | 1/1995 | Masse | 30/340 |

FOREIGN PATENT DOCUMENTS

0684470  4/1964  Canada .................................. 606/167

OTHER PUBLICATIONS

R. M. Zollinger and R. M. Zollinger, Jr., Atlas Of Surgical Operations, MacMillan Publishing Co., (4th ed. 1975), p. 22–23.
Aesculap, Inc., General Catalog, "Scalpels Blades and Handles", pp. 57–63 (1992).
Product Brochure, "Pilling", Pilling Co., pp. V and 276, circa 1994.
Baxter Healthcare Corporation, Surgical Armamentarium, pp. B1–B5, circa 1992.
American College of Surgeons Bulletin, Jan. 1995, vol. 80, No. 1, cover and title page.

Primary Examiner—Michael Powell Buiz
Assistant Examiner—Patrick W. Rasche
Attorney, Agent, or Firm—Nicola A. Pisano; Fish & Neave

[57] ABSTRACT

A scalpel handle is provided having the physical and ergonomic characteristics of a conventional surgical scalpel handle, but which houses a retractable blade support adapted for engaging scalpel blades having standard mounting posts. The scalpel blade is extended and retracted by the surgeon's index finger as a natural part of the motion of receiving and handing off the scalpel handle, which features few moving parts to thereby provide ease of disassembly and sterilization. Methods are also provided for replacing scalpel blades that are essentially the same as used for conventional non-retractable scalpel handles.

17 Claims, 3 Drawing Sheets

SCALPEL HANDLE HAVING RETRACTABLE BLADE SUPPORT AND METHOD OF USE

FIELD OF THE INVENTION

The present invention relates generally to surgical knives and more particularly to scalpel handles that permit retraction of the blade within the handle.

BACKGROUND OF THE INVENTION

The increasing prominence of blood-borne infectious disease, including the HIV virus and hepatitis, has lead to increased concern by surgeons of the risks of contracting such disease by inadvertent cuts occurring during the routine handling of medical instruments, particularly scalpels.

In response to these concerns, scalpels having retractable blades or extensible guards have been developed, such as are described in U.S. Pat. Nos. 5,344,424, 5,330,493, 5,330,492, 5,292,329, 5,275,606, 5,258,001, 5,211,652 and 5,201,748. A disadvantage common to all of these and other previously known safety scalpels is that these designs have radically different shapes, handling and ergonomic characteristics from standard scalpels having non-retractable blades. Consequently, there is significant resistance to adopting these scalpel designs, notwithstanding their safety features, because such scalpels require significant changes from conventional surgical handling techniques.

For example, it is common for the scalpel blade to be changed during the course of an operation. This procedure is typically performed by a nurse, who removes the old blade, and engages the new one, using a forceps and a simple twisting motion. This standard procedure is taught in nursing schools as an important feature of handling surgical scalpels. By contrast, the retractable scalpels described in U.S. Pat. No. 5,201,748 to Newman et al., U.S. Pat. No. 5,258,001 to Corman, and U.S. Pat. No. 5,211,652 to Derbyshire, must be completely disassembled for the blade to be replaced, a non-standard time-consuming procedure that detracts from the nurses' ability to perform other tasks.

Other previously known safety scalpels, like those described in U.S. Pat. No. 5,344,424 to Roberts et al. and U.S. Pat. No. 5,330,493 to Haining do not even contemplate blade replacement, thus requiring the surgeon to have available and use several scalpels during the course of a single operation, at considerably higher cost than that of replacement blades alone.

U.S. Pat. No. 5,342,379 to Volinsky describes a safety scalpel wherein the scalpel blade is loaded in a disposable cartridge. Apart from the inability to replace the blade, the peculiar shape of the cartridge needed to accommodate the retraction mechanism of that patent provides the surgeon with little tactile ability to determine the proper orientation of the scalpel. Consequently, the surgeon must actually divert his or her eyes from the surgical field to confirm that the scalpel is being held with an appropriate orientation.

Yet another drawback of many previously known safety scalpel designs, including those described in the Newman et al., Roberts et al., Corman and Derbyshire patents, is the unnatural location of the knobs or latches used to actuate the retractable feature of these scalpels. In particular, the side-mounted locations of the actuators in these scalpels may require an unnatural or awkward motion of the thumb to extend the scalpel blade and also may require departure from conventional scalpel gripping points, for example, as taught in R. M. Kirk, BASIC SURGERY TECHNIQUES, Churchill Livingstone Publishers (3rd. ed. 1989), at pp. 5–6 and 9–11, and R. M. Zollinger and R. M. Zollinger, Jr., ATLAS OF SURGICAL OPERATIONS, MacMillan Publishing Co., (4th ed. 1975), at p. 22, which are incorporated herein by reference. Thus, previously known retractable scalpels require considerable effort by the surgeon to master effective use.

The above-noted ergonomic considerations also apply to scalpel blades having retractable sheaths, as described, for example, in U.S. Pat. No. 5,275,606 to Abidin et al and U.S. Pat. No. 5,292,329 to Werner. When retracted, the sheaths described in those patents cover the distal portion of the handle, thus requiring the surgeon to hold the scalpel by gripping the sheath. This mode of gripping the scalpel is expected to interfere with the surgeons' sense of touch, and it is therefore expected that the retractable sheaths described in those patents will receive only limited acceptance in the surgical community.

Yet another disadvantage of previously known safety scalpels is the use of multiple internal components, including buttons, springs, etc., for example, as shown in the above-mentioned Werner, Haugen and Newman et al. patents. For disposable devices, such complicated designs may lead to unreliability, and high manufacture and assembly costs, which are ultimately passed on to the consumer. For reusable devices, complicated designs may increase dramatically the effort required to disassemble the devices to ensure adequate cleaning and sterilization.

In view of the foregoing, it would be desirable to provide a scalpel handle having the physical and ergonomic characteristics of a standard non-retractable scalpel handle, but which provides a retractable blade support member. In particular, it would be desirable to provide a scalpel handle having the approximate external physical dimensions, weight and balance of commonly used previously known scalpel handles, e.g., such as the well-known Bard-Parker® scalpel handles, marketed by Becton-Dickinson Company, AcuteCare Division, Franklin Lakes, N.J., Aesculap, Inc., South San Francisco, Calif., as B-P® Surgical Handle Nos. 3 and 4, Part Nos. BB 73, BB 75 C, BB 84, BB 84 C, BB 88 and BB 89, and Pilling Co., Fort Washington, Pa., as Part Nos. 35-2950 through 35-2954, all of which are incorporated herein by reference. The Bard-Parker® scalpel handle has been the most commonly used medical scalpel for almost 100 years, as depicted by, for example, the cover of *American College of Surgeons Bulletin*, Jan. 1995, Vol. 80, No. 1, also incorporated herein by reference.

It further would be desirable to provide a scalpel handle having a retractable blade support member that accommodates a standard scalpel blade mounting post, and methods of use of such a scalpel, so that the blade may be replaced during use in essentially the same manner as conventional with scalpel handles.

It also would be desirable to provide a scalpel handle having a retractable blade support that includes an actuating tab that is positioned to permit the surgeon to extend and retract the scalpel blade, while holding the scalpel in a manner nearly identical to that currently employed when using standard non-retractable scalpels.

It also would be desirable to provide a scalpel handle having a retractable blade support that employs few working components and that is repeatedly sterilizable, or which includes a sterilizable main component and a disposable subcomponent.

SUMMARY OF THE INVENTION

In view of the foregoing, it is an object of this invention to provide a scalpel handle having the physical and ergonomic characteristics of commonly used previously known scalpel handles, such as Bard-Parker® No. 3 or No. 4 scalpel handles, but which provides a blade support member that can be retracted within the scalpel handle to shield the blade.

It is another object of this invention to provide a scalpel handle having a retractable blade support that accommodates a standard scalpel blade mounting post, and methods of use, so that the blade may be replaced during use in essentially the same manner as conventionally performed with standard non-retractable scalpel handles.

It is yet another object of the present invention to provide a scalpel handle having a retractable blade support that includes an actuating tab that is positioned to permit the surgeon to extend and retract the scalpel blade while holding the scalpel in a manner nearly identical to that currently employed when using standard non-retractable scalpels.

It is a still further object of the present invention to provide a scalpel handle having a retractable blade support that is repeatedly sterilizable, that includes a sterilizable main component and a disposable subcomponent, or that is completely disposable.

These and other objects of the invention are accomplished in accordance with the principles of the invention by providing a scalpel handle having the external characteristics, weight and feel of the most commonly and currently used scalpels, such as Bard-Parker® scalpel handles, but which houses a retractable blade support adapted for engaging scalpel blades having standard mounting posts.

In a preferred illustrative embodiment of a scalpel handle constructed in accordance with the present invention, the scalpel handle has the approximate weight and feel of a standard non-retractable No. 3 Bard-Parker® scalpel handle. The scalpel handle includes a unitary blade carrier disposed in an interior chamber of the handle, a first leg of the blade carrier forming a support member adapted for engaging a scalpel blade having a standard mounting post, and a second leg that forms a tab for extending and retracting the support member (and an engaged blade) from the interior chamber. The tab of the blade carrier extends through a slot in the upper surface of the handle, so that extension and retraction of the blade may be accomplished using the index finger, while only minimally altering the way in which the surgeon normally handles the scalpel, for example, when passing it off to a nurse.

Further features of the invention, its nature and various advantages will be more apparent from the accompanying drawings and the following detailed description of the preferred embodiments.

DETAILED DESCRIPTION OF THE PREFERRED EMBODIMENTS

The present invention relates generally to scalpel handles having the approximate external dimensions and ergonomic characteristics of standard medical scalpel handles, but which further provide for selectively retracting the scalpel blade during handling of the scalpel. In the exemplary embodiments of the scalpel handle of the present invention, the scalpel handle is described as having the approximate external dimensions, weight and feel of a standard non-retractable scalpel handle of a No. 3 or No. 4 scalpel of the well-known Bard-Parker® design, as marketed by several manufacturers, including Becton-Dickinson Company, Franklin Lakes, N.J., Aesculap, Inc., South San Francisco, Calif., and Pilling Co., Fort Washington, Pa.

It will of course be understood by those skilled in the relevant arts that these exemplary embodiments of the invention in no way limit the intended use of the scalpel handle of the present invention, and that the present invention could be implemented in other widely-accepted scalpel handle configurations. In addition, while the scalpel handle of the present invention is described with reference to accepting scalpel blades having standard mounting posts of the Bard-Parker® type, it is equally applicable to less common scalpel blade mounting post designs.

Figure 1A:
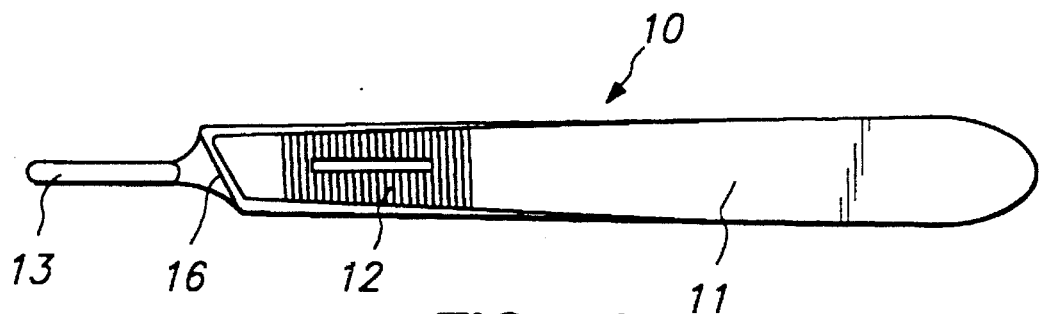
FIGS. 1A and 1B are side and plan views of an illustrative prior art non-retractable blade scalpel handle.
Figure 1B:
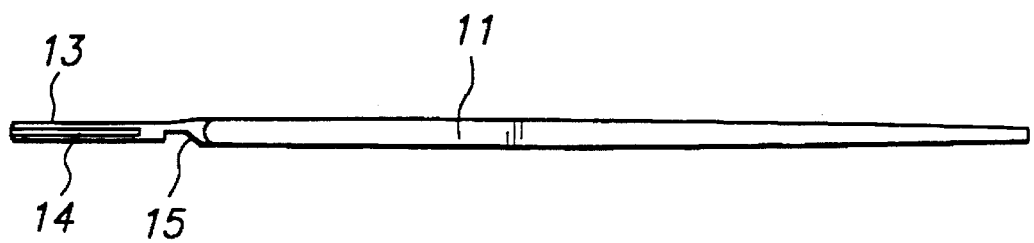

Referring to FIGS. 1A and 1B, prior art non-retractable scalpel handle 10 is described. Scalpel handle 10 is illustratively a No. 3 Bard-Parker® scalpel handle, part no. BB 73, available from Aesculap, Inc., and is depicted approximately in actual size in FIGS. 1. Scalpel handle 10 includes handle portion 11 having serrations 12 and integrally formed blade receiving member 13. Blade receiving member 13 includes grooves 14 on the upper and lower surfaces of blade receiving member 13, indentation 15 and angled shoulder 16.

As is conventional, a scalpel blade used with handle 10, for example, a No. 11 blade (see FIG. 3), includes a key-shaped slot and an angled rear edge, which permit the scalpel blade to be disposed on blade receiving member so that the narrow portion of the key-shaped slot is engaged in groove 14, while the angled rear edge of the slot abuts angled shoulder 16. Indentation 15 permits the proximal portion of the blade to lay approximately in the plane of groove 14.

Figure 2A:
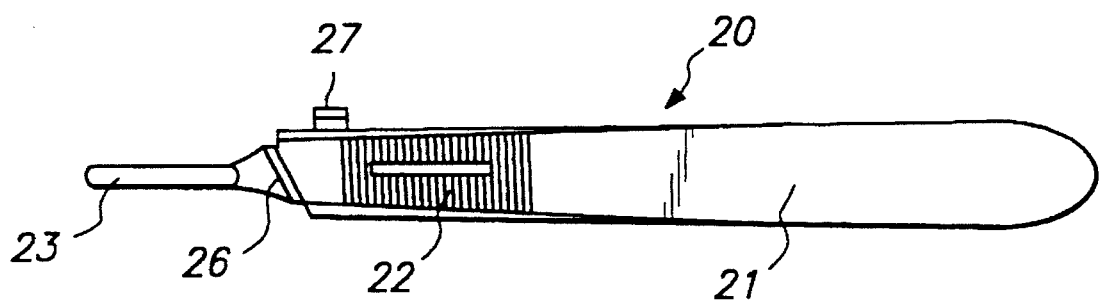
FIGS. 2A and 2B are side and plan views of an illustrative embodiment of a retractable blade scalpel handle constructed in accordance with the present invention.
Figure 2B:
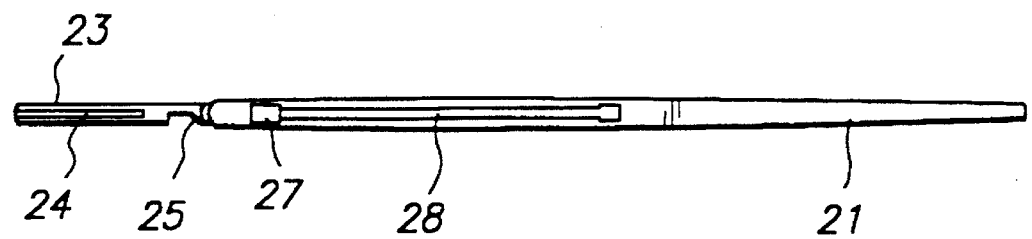

Referring now to FIGS. 2A and 2B, scalpel handle 20 constructed in accordance with the present invention is described. Scalpel handle 20 (depicted in approximately actual size in FIGS. 2) has approximately the external size, weight and feel of scalpel handle 10, and likewise includes handle portion 21, serrations 22 for gripping the scalpel handle, blade receiving member 23, grooves 24, indentation 25 and angled shoulder 26.

In particular, scalpel handle 20 has the approximate length, height and weight of a standard, non-retractable scalpel handle. While the width of scalpel handle is preferably about the same as for a corresponding standard non-retractable scalpel handle, the width of scalpel handle 20 may be up to about one-half again as wide, to accommodate retraction of the scalpel blade and blade receiving member, described hereinbelow. Any increase in weight associated with this greater width of the scalpel handle, however, is offset by the material removed to create the interior chamber. Thus, the overall weight and feel of scalpel handle 20 is approximately the same as for a corresponding standard non-retractable scalpel handle.

In accordance with the present invention, scalpel handle 20 further includes tab or button 27 extending through slot 28 in the upper surface of handle portion 21. Blade receiving member 23 is operatively connected to button 27 so that blade receiving member 23 (and any blade disposed thereon) may be retracted within handle portion 21, as described hereinbelow.

Figure 3:
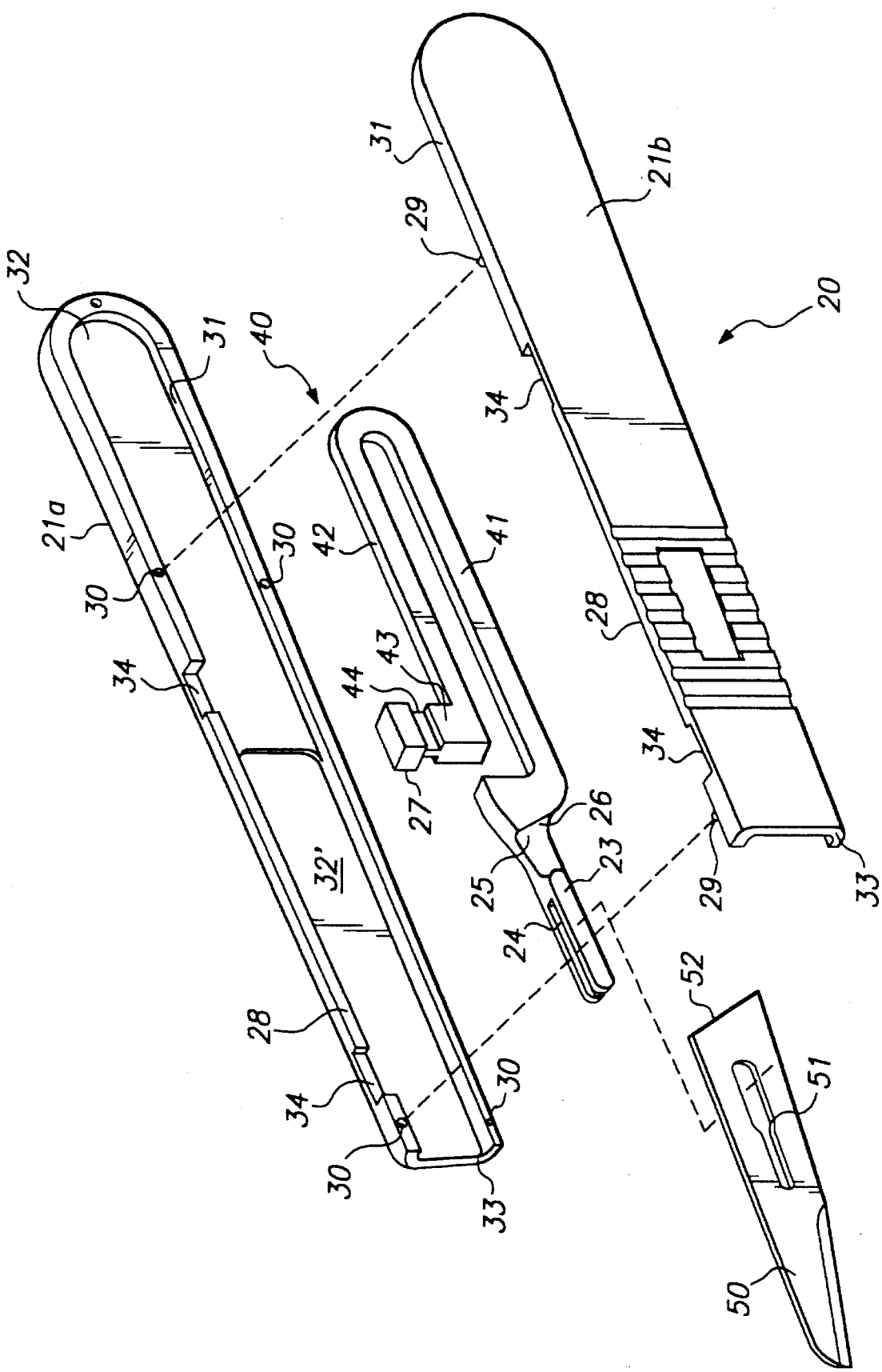
FIG. 3 is an exploded perspective view of the scalpel handle of FIGS. 2 shown with a conventional No. 11 scalpel blade.

Referring now to FIG. 3, a first illustrative embodiment of the internal detail of scalpel handle 20 of FIGS. 2 is described. Handle portion 21 comprises first and second halves 21a and 21b that may be detachably coupled together by inserting pins 29 into holes 30. Pins 29 and holes 30 are dimensioned so that halves 21a and 21b frictionally interengage when the halves are pressed together, but may be pried apart with a low force using a tool, for example, a screwdriver. Pins 29 and holes 30 therefore provide sufficient force to retain halves 21a and 21b coupled together when during use, but permit scalpel handle 20 to be readily disassembled for cleaning and sterilization.

Each of halves 21a and 21b include a rim portion 31 that surround and define a chamber 32 when the two halves are pressed together. Rim 31 is omitted from distal faces 33 of halves 21a and 21b to provide a distal opening in chamber 32, through which blade receiving member is selectively extended, as described below. Rim 31 also has a reduced height along the upper surfaces of halves 21a and 21b to form slot 28, with a further reduction at the distal and proximal ends of slot 28 to form engagement holes or notches 34. Distal portion 32' of chamber 32 may also be wider than the proximal portion of chamber 32 to permit blade receiving member 23 to be fully withdrawn into chamber 32.

As shown in FIG. 3, blade receiving member 23 is disposed from first leg 41 of an approximately U-shaped blade carrier 40. Button 27 is disposed on second leg 42 of U-shaped blade carrier 40 and includes engagement block 43 and narrowed portion 44. As will be apparent from FIG. 3, U-shaped blade carrier 40 is slidably disposed in chamber 32 so that blade receiving member 23 (and any scalpel blade disposed thereon) are fully retracted within chamber 32 when the button 27 is moved to a proximal-most position, while blade receiving member 23 (and any scalpel blade disposed thereon), including indentation 25 and angled shoulder 26 are fully extended from chamber 32 when button 27 is moved to its distal-most position.

In particular, blade carrier 40 is disposed in chamber 32 within halves 21a and 21b so that an upper surface of first leg 42 abuts against rim 31 along the top of chamber 32, while a lower surface of second leg 42 abuts against rim 31 along the bottom of chamber 32. This arrangement permits blade carrier to move slidingly in the proximal and distal directions, while reducing lateral and up/down movement of blade carrier 40 within chamber 32, thus providing the necessary degree of stability for use in surgery.

Narrowed portion 44 of button 27 is sized to permit it to slide through slot 28 when button 27 is depressed slightly, while engagement block 43 locks into position in one of engagement holes 34 when blade carrier 40 is moved to either end of slot 28 and button 27 is released. By way of example, if slot 28 is 28 mils wide, engagement holes 44 may be 45 mils wide, while narrowed portion 44 may be 25 mils wide, leaving a clearance of about 3 mils between the width of slot 28 and narrowed portion 43. Accordingly, button 27 (and thus blade carrier 40 and blade receiving portion 23), positively locks into position only at the ends of its travel in slot 28, thereby preventing inadvertent retraction or extension of the scalpel blade during handling.

As described above, blade receiving portion 23 includes grooves 24, indentation 25, and angled shoulder 26 for accepting standard Bard-Parker® scalpel blade 50. Such scalpel blades, of which a No. 11 blade is illustrated in FIG. 3, and includes a mounting post having key-shaped slot 51, and angled rear surface 52. In particular, when blade carrier 40 is locked in its distal-most (extended) position, scalpel blade 50 may be attached to or removed from blade receiving member 23 using standard techniques. Thus, nurses installing or replacing blades on scalpel handle 20 of the present invention will find that no special attention or handling is required beyond that associated with installing or replacing scalpel blades on standard non-retractable scalpel handles, other than a step of extending blade receiving member 23.

Scalpel handle 20 of the illustrative embodiment of FIG. 3 may be constructed of materials commonly used in medical scalpels so as to give the completed scalpel handle 20 the overall weight, feel and handling characteristics of a non-retractable scalpel handle. For example, halves 21a and 21b may comprise a steel or magnesium alloy, while U-shaped member 40 is preferably integrally formed from a sturdy and resilient material, e.g., a steel alloy, that enables button 27 and second leg 42 to be elastically deflected towards first leg 41 when button 27 is depressed. Construction of halves 21a, 21b and blade carrier 40 from materials typically used in medical instruments enables scalpel handle 20 to be disassembled for repeated cleaning and resterilization.

Alternatively, halves 21a and 21b may be formed, for example, of a rigid plastic material, e.g., an injection molded plastic, while blade carrier 40 may be formed of a sturdy and resilient material, e.g., a steel alloy. In this manner, halves 21a and 21b may be disposed of after a single use, while blade carrier 40 may be cleaned and resterilized for repeated use. Such a semi-disposable version eliminates the necessity to clean or resterilize halves 21a, 21b, while reducing the number of parts that must be tracked during cleaning and sterilization for re-use, since only the blade carrier is re-used. In yet a further alternative, blade carrier 40 itself could be disposable, as well as halves 21a, 21b.

Figure 4:
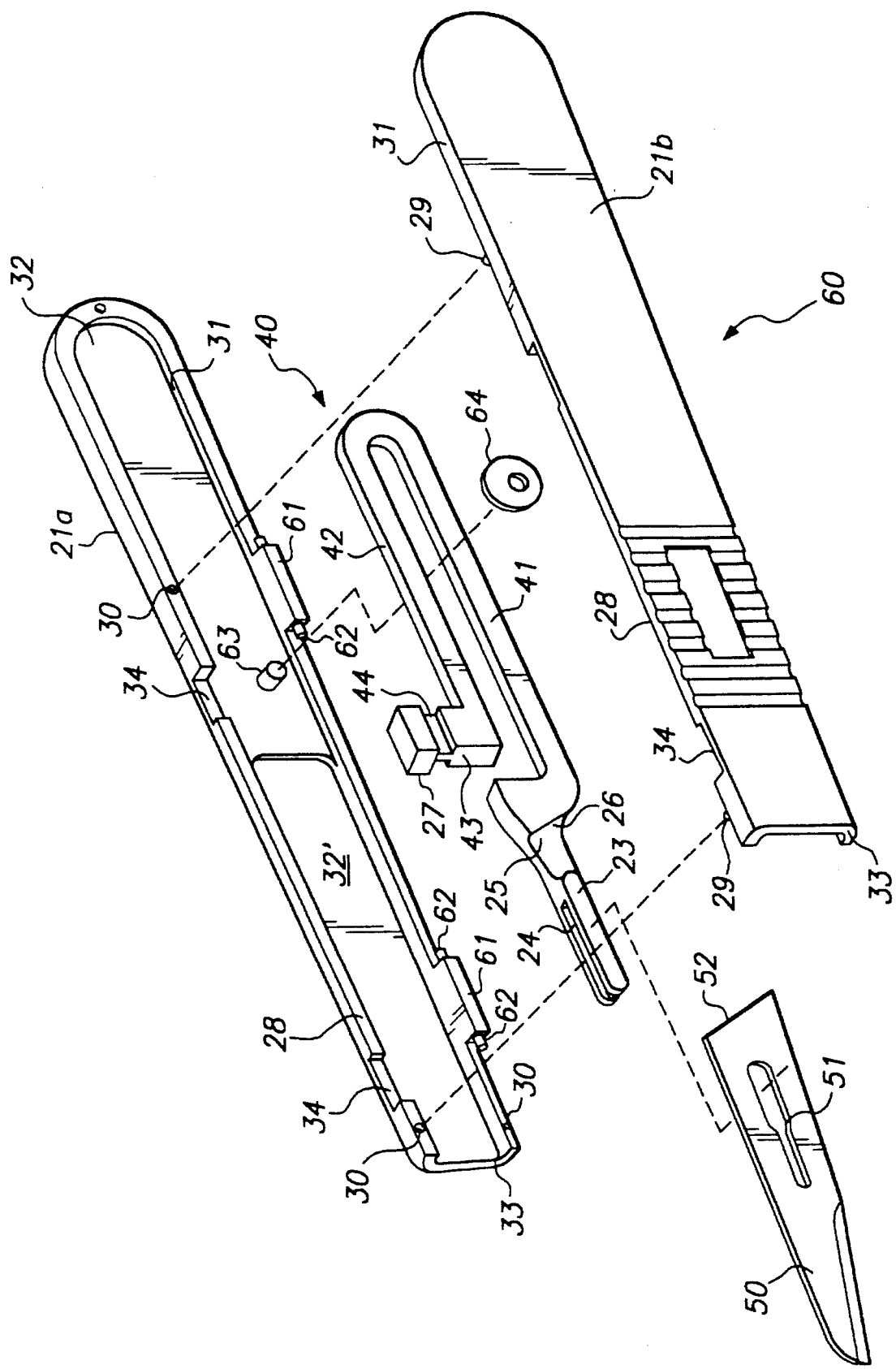
FIG. 4 is an exploded perspective view of an alternative embodiment of the scalpel handle of FIGS. 2.

Referring now to FIG. 4, an alternative embodiment of scalpel handle 60 similar to that of FIGS. 2 and 3 is described. Portions of scalpel handle 60 that correspond to like portions of scalpel handle 30 of FIG. 3 are indicated by similar reference numerals in FIG. 4.

Scalpel handle 60 differs from scalpel handle 20 of FIG. 3 in that it includes further features that permit the scalpel handle to be easily opened for cleaning and sterilization, while remaining a one-piece assembly. In particular, scalpel handle 60 includes hinges 61 with pins 62 extending from rim 31 of half 21a that are engaged in indentations (and holes) in rim 31 of half 21b (not shown). Pins 29 and holes 30 are located along the upper portions of rim 31 for detachably interengaging the halves 21a and 21b.

Hinges 61 permit the halves to be pried open and then swung apart for cleaning and sterilization, without creating two separate pieces; thus reducing the potential for loss of one or both pieces. Hinges 61 also obviate the need to carefully align the pins and holes as required for the embodiment of FIG. 3, since the pins and holes of the embodiment of FIG. 4 are kept in proper alignment by the hinges.

In addition, scalpel handle 60 includes pin 63 disposed between legs 41 and 42 of blade carrier 40 that, in conjunction with washer 64, retains blade carrier 40 in position on half 21a when half 21b is swung away. Washer 64 may be permanently fastened to pin 63, for example, by press fitting or peening, or removably fastened (e.g., a friction fit washer) so that blade carrier may be slidably moved on pin 63 to its proximal-most and distal-most positions, but retained by washer 64 from removal from half 21a.

Pin 63 is preferably located eccentrically in washer 64, i.e., so that it is closer to first leg 41 of blade carrier 40 than second leg 42, so that pin 63 will not interfere with downward deflection of second leg 42. Accordingly, scalpel handle 60 of FIG. 4 provides an arrangement that may be readily opened for repeated for cleaning and re-sterilization, without risk of loss of-any of the components of the device.

Operation of the scalpel handle as described with respect to FIGS. 2–4 is apparent from the above description and may be accomplished by the surgeon using his index finger to locate and urge button 27 in a proximal or distal direction. Because button 27 is located along the top edge of the scalpel handle, it is in a natural position for the surgeon to depress and slide it distally with his or her index finger when using the scalpel.

As described in the above-incorporated pages of the surgical texts, positioning the index finger along the upper edge of the scalpel handle is part of the standard technique of using such instruments. Thus, the scalpel handle of the present invention does not require the surgeon to divert his or her eyes from the surgical site to determine the status of the scalpel blade. Rather, the location of button 27 permits the surgeon to locate it and instantly determine whether the scalpel blade is extended or retracted, as well as to extend or retract the scalpel blade, without disturbing the conventional way in which a surgeon holds the scalpel. And because the scalpel handle of the present invention has the ergonomic characteristics (e.g., weight, feel) of conventional non-retractable scalpel handles, it is expected that scalpel handles in accordance with the present invention will find greater acceptance in the surgical community than has heretofore been possible with previously known safety scalpels.

While the present invention has been illustratively described with respect to a No. 3 Bard-Parker® type scalpel handle, it will be readily apparent to one of skill in the art that the present invention may be adapted for use in other scalpel handle designs, such as the BB 75C (No. 3) and BB 84, BB 85 C, BB 88 and BB 89 (all No. 4) scalpel handles marketed by Aesculap, Inc.

Moreover, while preferred illustrative embodiments of the present invention are described above, it will be obvious to one skilled in the art that various changes and modifications may be made therein without departing from the invention and it is intended in the appended claims to cover all such changes and modifications which fall within the true spirit and scope of the invention.

What is claimed is:

1. A scalpel handle adapted for use with a scalpel blade having a mounting post, the scalpel handle comprising:
   a housing having a proximal end and a distal end, the housing defining a chamber having an upper surface and an opening at the distal end, the housing having a portion defining a slot in the upper surface, and proximal and distal notches formed in the slot;
   a blade carrier slidably disposed within the chamber and comprising a first leg having proximal and distal portions, a second leg having proximal and distal portions, and means for flexibly joining the proximal portions of the first and second legs, the distal portion of the first leg defining a support member adapted for replaceably engaging a scalpel blade mounting post, the distal portion of the second leg defining a tab to selectively engage either the distal notch, to extend the support member from the chamber, or the proximal notch, to retract the support member and a replaceably engaged scalpel blade within the chamber.

2. The scalpel handle as defined in claim 1 wherein the scalpel handle has about the shape, weight and feel of a standard No. 3 surgical scalpel.

3. The scalpel handle as defined in claim 1 wherein the scalpel handle has about the shape, weight and feel of a standard No. 4 surgical scalpel.

4. The scalpel handle as defined in claim 1 wherein the support member is adapted for engaging a scalpel blade having a mounting post, the mounting post including a key-shaped slot, a proximal portion, and an angled rear face, the support member further comprising a portion defining at least one groove adapted for engaging the key-shaped slot, an indentation for accepting the proximal portion of the scalpel blade, and an angled shoulder against which the rear face abuts.

5. The scalpel handle as defined in claim 1 wherein the scalpel handle may be readily disassembled for cleaning and sterilization.

6. The scalpel handle as defined in claim 5 wherein the blade carrier comprises an unitary element and the housing comprises first and second halves and means for removably joining the first and second halves together.

7. The scalpel handle as defined in claim 6 wherein the support member is adapted for engaging a scalpel blade having a mounting post, the mounting post including a key-shaped slot, a proximal portion, and an angled rear face, the support member further comprising a portion defining at least one groove adapted for engaging the key-shaped slot, an indentation for accepting the proximal portion of the scalpel blade, and an angled shoulder against which the rear face abuts.

8. The scalpel handle as defined in claim 6 wherein the means for removably joining comprises a plurality of pins and a plurality of holes, the plurality of pins removably interengaging the plurality of holes.

9. The scalpel handle as defined in claim 6 wherein the means for removably joining comprises at least one hinge.

10. The scalpel handle as defined in claim 5 wherein the blade carrier has substantially a U-shaped configuration, the first and second legs forming first and second legs of the U-shape.

11. The scalpel handle as defined in claim 5 wherein the blade carrier comprises a unitary element and the housing comprises at least one disposable unit.

12. The scalpel handle as defined in claim 11 wherein the support member is adapted for engaging a scalpel blade having a mounting post, the mounting post including a key-shaped slot, a proximal portion, and an angled rear face, the support member further comprising a portion defining at least one groove adapted for engaging the key-shaped slot, an indentation for accepting the proximal portion of the scalpel blade, and an angled shoulder against which the rear face abuts.

13. The scalpel handle as defined in claim 11 wherein the blade carrier has substantially a U-shaped configuration, the first and second legs forming first and second legs of the U-shape.

14. The scalpel handle as defined in claim 11 wherein the disposable molded unit is formed of an injection molded plastic.

15. The scalpel handle as defined in claim 1 wherein the scalpel handle is completely disposable.

16. The scalpel handle as defined in claim 15 wherein the housing is formed of an injection molded plastic.

17. A method of replacing scalpel blades used in conjunction with a scalpel handle comprising a blade carrier slidably disposed within a housing, the housing defining a proximal notch and distal notch, the blade carrier comprising a first leg having proximal and distal portions, a second leg having proximal and distal portions, and means for flexibly joining the proximal portions of the first and second legs, the distal portion of the first leg defining a support member adapted for replaceably engaging a scalpel blade mounting post, the distal portion of the second leg defining a tab that selectively engages either the distal notch, to extend the support member from the housing, or the proximal notch, to retract the support member and a replaceably engaged scalpel blade within the housing, in which a used scalpel blade is replaced by a new scalpel blade, each of the used and new scalpel blades having a mounting post including a key-shaped slot, a proximal portion, and an angled rear face, the support member comprising a portion defining at least one groove adapted for engaging the key-shaped slot, an indentation for accepting the proximal portion of the scalpel blade, and an angled shoulder against which the rear face abuts, the method comprising steps of:

extending the support member and the used scalpel blade from within the scalpel handle;

gripping the used scalpel blade with a pair of forceps;

twisting the used scalpel blade so that the rear face and proximal portion disengage the angled shoulder and indentation;

pulling the used scalpel blade in a distal direction to disengage the key-shaped slot from the at least one groove;

disposing of the used scalpel blade;

gripping the new scalpel blade;

sliding the new scalpel blade onto the support member so that the key-shaped slot engages the at least one groove; and twisting the new scalpel blade so that the rear face and proximal portion engage the angled shoulder and indentation.

* * * * *